United States Patent [19]

Wagner et al.

[11] Patent Number: 5,739,393
[45] Date of Patent: Apr. 14, 1998

[54] PROCESS FOR THE PREPARATION OF POLYMERS WITH RECURRING SUCCINYL UNITS

[75] Inventors: Paul Wagner, Düsseldorf; Frank Döbert, Köln; Torsten Groth, Odenthal; Winfried Joentgen, Köln, all of Germany

[73] Assignee: Bayer AG, Leverkusen, Germany

[21] Appl. No.: 802,992

[22] Filed: Feb. 21, 1997

[30] Foreign Application Priority Data

Sep. 6, 1996 [DE] Germany .................. 196 36 190.7

[51] Int. Cl.⁶ .................................................. C08G 63/44
[52] U.S. Cl. ................................... 562/553; 528/363
[58] Field of Search ........................ 562/553; 528/363

[56] References Cited

U.S. PATENT DOCUMENTS

| | | | |
|---|---|---|---|
| 4,839,461 | 6/1989 | Boehmke | 528/363 |
| 5,288,783 | 2/1994 | Wood | 525/418 |
| 5,466,779 | 11/1995 | Ross | 528/363 |
| 5,548,036 | 8/1996 | Kroner et al. | 525/419 |
| 5,612,447 | 3/1997 | Freeman et al. | 528/328 |

FOREIGN PATENT DOCUMENTS 43 00 020  1/1993  Germany .

OTHER PUBLICATIONS

Harada, Polycondensation of Thermal Precursors of Aspartic Acid, J. Org. Chem., vol. 24, pp. 1662–1666 (Nov., 1959).

*Primary Examiner*—Terressa Mosley
*Attorney, Agent, or Firm*—Connolly & Hutz

[57] ABSTRACT

Polymers with recurring succinyl units are prepared by reaction of maleic anhydride, maleic acid or fumaric acid with condensed liquid ammonia and polymerization of the resulting reaction product.

20 Claims, No Drawings

PROCESS FOR THE PREPARATION OF POLYMERS WITH RECURRING SUCCINYL UNITS

The invention relates to a process for the preparation of polymers with recurring succinyl units.

The preparation and use of polyaspartic acid (PAA) and its derivatives has been the subject of numerous publications and patents for a long time.

According to J. Org. Chem., 24, pages 1662–1666, (1959), polysuccinimide-(PSI), which is called "auhydropolyaspartic acid" therein, is obtained by thermal polycondensation of maleamic acid or malic acid monoammonium salt as temperatures of up to 200° C. The polymer yields were 75% to 79% at 200° C. Malic acid, maleic anhydride, fumaric acid and asparagine are furthermore mentioned as possible starting substances.

U.S. Pat. No. 4,839,461 (=EP-A 0 256 366) describes the preparation of polyaspartic acid from maleic anhydride, water and ammonia. Maleic arkhydride is reacted in an aqueous medium with the addition of concentrated ammonia solution and is then polymerized. U.S. Pat. No. 5,288,783 describes the preparation of PSI from maleic anhydride and ammonia at higher temperatures and the hydrolysis to give PAA.

DE-A 43 00 020 relates to the preparation of polymers of aspartic acid by thermal condensation of half-amides of maleic acid or fumaric acid or of ammonium salts of the half-amides. The reaction is carried out at temperatures above the melting point of maleic anhydride with gaseous ammonia.

A disadvantage of the known processes is, inter alia, that the removal of the water in the polymerization step can present difficulties.

The present invention relates to a process for the preparation of polymers with recurring succinyl units, which comprises reacting maleic anhydride, maleic acid and/or fumaric acid, if appropriate in the presence of comonomers, with condensed liquid ammonia and polymerizing and, if appropriate, hydrolyzing the resulting reaction product.

Surprisingly, the reaction of, for example, maleic anhydride can be carried out in liquid ammonia, where vapor cooling by the evaporating ammonia can be used as a simple and efficient method of temperature control.

The polymers prepared according to the invention preferably contain recurring succinyl units having at least one of the following structures

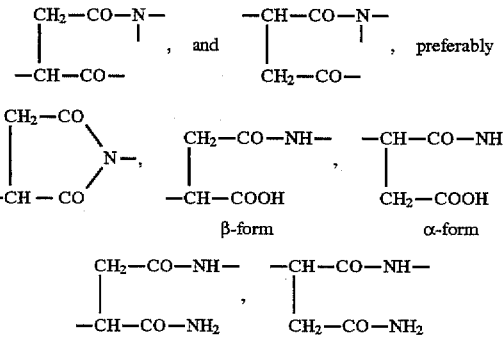

or a salt thereof.

The polymers can additionally contain iminodisuccinate traits in preferably at least one of the following structures:

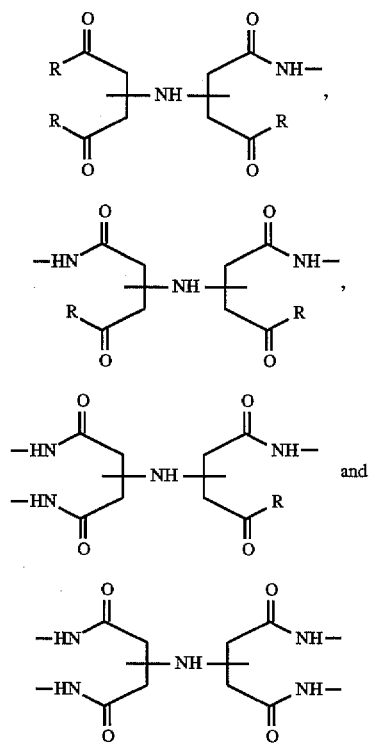

in which R is OH, ON⁻NH$_4$ or NH$_2$.

The polymer prepared preferably shows chain lengths or molecular lengths according to analyses by gel permeation chromatography (Mw) of 500 to 10,000, preferably 500 to 5,000, particularly preferably 700 to 4,500, depending on the reaction conditions, for example the residence time and temperature of the thermal polymerization. Based on the groups

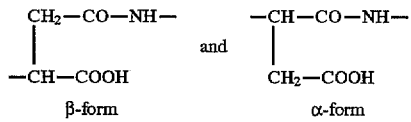

(recurring aspartic acid units), preferably at least 50%, in particular at least 70%, are present in the β-linked form.

If iminodisuccinate units are present, they can be present in the polymer in random distribution or, preferably, as an end group. Based on the sum of all the recurring units, in a preferred embodiment the iminodisuccinate unit is present to the extent of at least 0.1 mol %. The molar ratio of the iminodisuccinate units incorporated in the polymer to the sum of all the monomer units incorporated in the polymer is preferably 0.1 mol % to 99 mol %, preferably 1 mol % to 50 mol %, particularly preferably 2 mol % to 25%.

The polymer can additionally contain further recurring units, by a suitable reaction procedure and choice of the educts, for example a) malic acid units of the formula

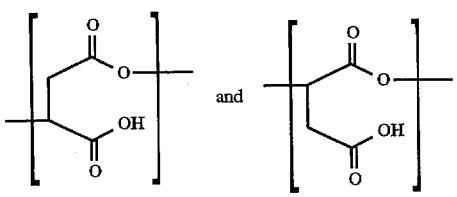

b) maleic acid and fumaric acid units of the formula

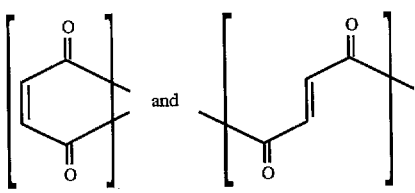

The educts can be employed individually or as mixtures, in bulk or in solution. If appropriate, the polymers according to the invention can be present as the free acid or as a salt, and preferred salts are, for example, alkaline metal and ammonium salts.

Maleic anhydride or its derivatives are employed as a melt in a preferred embodiment.

If appropriate, the reaction of the educts can be carried out in the presence of a cosolvent. Suitable cosolvents are lower alcohols, polar aprotic solvents, such as dimethylformamide, N-alkylpyrrolidones, sulfolane, acetone, polyalkylene glycols, polyalkylene glycol monoalkyl ethers and polyalkylene glycol dialkyl ethers.

Supercritical gases, such as, for example, carbon dioxide, are also suitable.

In a preferred embodiment, the educts are molten maleic arthydride and ammonia.

Preferably, molten maleic anhydride is passed into a reactor filled with liquid ammonia. The temperature of the maleic anhydride here is 60° to 100° C. The reaction of the maleic arthydride preferably takes place at temperatures between 60° and 100° C. under a pressure of 26 to 64 bar. The molar ratio of maleic arthydride and ammonia is preferably at least 1:4, and is preferably 1:4 to 1:500. The excess of ammonia is of particular advantage since the reaction of the anhydride with the ammonia is a very fast and highly exothermic reaction. The heat of reaction can be removed in a simple manner without additional diluents by the evaporation of ammonia. Because of the excess of ammonia, for example, the ammonium salt of maleamic acid can be formed.

It is possible, for example, for intermediate products such as maleic acid diammonium salt or maleamic acid ammonium salt to be prepared from the abovementioned educts in a separate process step and then to be subjected to discontinuous or continuous thermal polymerization in bulk or in suitable solvents.

The invention therefore also relates to a process for the preparation of non-polymerized nitrogen compounds of a $C_4$-carboxylic acid, which comprises reacting maleic anhydride, maleic acid and/or fumaric acid with condensed liquid ammonia to give a low molecular weight product. This can be, for example, an amide, imide or ammonium salt, in particular the mono- or diammonium salt of maleic acid, maleamic acid, aspartic acid, iminodisuccinic acid, iminodisuccinamic acids or asparagine.

The polymerization of the reaction product is in general carried out at temperatures between 100° C. and 350° C., preferably between 120° C. and 250° C., particularly preferably between 120° C. and 220° C. The residence time is preferably between 1 second and 600 minutes, preferably 5 seconds to 180 minutes, particularly preferably 10 seconds to 150 minutes. However, for example, it can also be carried out differently, for example with microwaves.

All apparatuses which, with a narrow distribution of the residence time, allow the necessary minimum residence time for polymerization and at the same time at least partial evaporation of the solvent and of the water formed during the reaction are in principle suitable for the thermal polymerization.

Preferred devices for the thermal polymerization are thus all apparatuses which show a defined residence time with a narrow distribution of the residence time for the solid or highly viscous liquid phase and at the same time allow good temperature control due to at least partial evaporation of the solvent (organic solvent and/or water) and/or of the water of reaction formed during the polymerization. Such preferred devices can be, for example a) fluidized bed reactors b) high viscosity reactors (for example screw, List reactor)

c) dryer (for example paddle dryer, spray dryer)

If the polymerization products are ring systems, these can be converted into an open-chain system, for example a PAA-containing copolymer salt, by reaction with a base, if appropriate in the presence of water. This conversion of, for example, PSI-containing into PAA-containing copolymers is effected in a suitable device by hydrolysis. A pH of between 5 and 14 is preferably suitable here in the aqueous system. In a particularly preferred form, a pH of 7 to 12 is chosen, in particular by addition of a base. Suitable bases are alkali metal and alkaline earth metal hydroxides or carbonates, such as, for example, sodium hydroxide solution, potassium hydroxide solution, sodium carbonate or potassium carbonate, ammonium and amines, such as triethylamine, triethanolamine, diethylamine, diethanolamine, alkylamines and the like.

The temperature during the hydrolysis is preferably in a range including up to the boiling point of the suspension or solution containing succinyl groups, and preferably 20° to 150° C. If appropriate, the hydrolysis is carried out under pressure. If appropriate, the hydrolysis is carried out with the addition of another monoethylenically unsaturated carboxylic acid derivative. Examples of suitable derivatives are maleic arthydride, maleic acid, citraconic acid, itaconic acid, aconitic acid, acrylic acid and fumaric acid.

Under the basic conditions of the hydrolysis, addition of the amino groups of the N-terminal end of the polymer molecule onto the monoethylenically unsaturated carboxylic acid derivative present in the salt form can take place.

Depending on the polymerization conditions, the primary polymerization products can also have ethylenically unsaturated end groups. It may therefore be expedient also to add, where appropriate, aminocarboxylic acids, for example glycine, aspartic acid, lysine, glutamic acid and the like, to the reaction mixture during the basic hydrolysis. Grafting of the polymer end groups is achieved by this measure.

The polymers are distinguished by an improved calcium-bonding capacity. They furthermore show complexing properties with respect to heavy metals such as, for example, copper, iron and the like. They can be used as an additive in low-phosphate and phosphate-free detergents and cleaning compositions. The polymers are builders for detergents and have the effect of reducing encrustation and graying on washed textile goods during the washing operation.

The polymers according to the invention furthermore inhibit and delay the precipitation of salts, in particular crystals, for example of calcium carbonate, calcium sulfate, calcium phosphate, barium sulfate and magnesium silicate, from aqueous solutions and are therefore suitable as water treatment agents. They can be added to the water in cooling circulations, evaporators or seawater desalination plants and injection waters for secondary oil production and water treatment in mining. They can furthermore be employed as agents for preventing deposits forming during evaporation of sugar juice.

On the basis of the complexing property with respect to the heavy metals, the copolymers can also be used as stabilizing agents for bleaching agents such as hydrogen peroxide in bleaching processes.

The copolymers according to the invention are to be classified as biologically degradable in accordance with the "OECD Guidelines for testing of chemicals (1981)".

EXAMPLE 297 g of liquid condensed ammonia were initially introduced into a 1.4 l autoclave with an attached condenser and heated to a temperature of 70° C., a pressure of 33 bar being established in the reaction vessel as a result. 90 g of liquid maleic anhydride were then pumped into the stirred tank reactor at T=70° C. and the mixture was stirred for 1 hour. After a reaction time of 1 hour at 70° C., the pressure was let down to 1 bar and the temperature was increased to 170° C. while gassing with nitrogen. The reaction time of the polymerization was 6 hours. The cooled reaction product was suspended in 200 ml of water and dissolved with 40% strength sodium hydroxide solution up to a pH of 8.5. The yield of the sodium salt of polyaspartic acid was 123 g. The weight-average of the molecular weights, determined by means of gel permeation chromatography, was about 1750 g/mol, and the β-content was about 70%.

We claim:

1. A process for the preparation of a polymer with recurring succinyl units, which comprises reacting maleic anhydride, maleic acid and/or fumaric acid with condensed liquid ammonia.

2. The process as claimed in claim 1, wherein maleic anhydride is reacted with condensed liquid ammonia.

3. The process as claimed in claim 1, wherein at least 4 mol of ammonia are employed per mol of maleic anhydride, maleic acid or fumaric acid.

4. The process as claimed in claim 1, wherein the reaction is carried out in liquid ammonia at 60° to 100° C. under a pressure of 26 to 64 bar.

5. The process as claimed in claim 1, wherein the polymerization is carried out at 100° to 350° C.

6. The process as claimed in claim 1, wherein the polymerization is achieved using microwaves.

7. The process as claimed in claim 1, wherein the heat of reaction formed during the reaction in the liquid ammonia is removed by vapor cooling by means of ammonia.

8. The process as claimed in claim 1, wherein the ammonia evaporated by the vapor cooling and the ammonia liberated during the polymerization are recycled.

9. The process as claimed in claim 1, wherein the resulting polymer has a molecular weight to 500 to 10,000 Mw as measured by gel permeation chromatography.

10. The process as claimed in claim 1, wherein the product obtained after the reaction is hydrolyzed with a base.

11. A process for the preparation of a low molecular weight nitrogen compound of a $C_4$-dicarboxylic acid, which comprises reacting maleic acid, maleic anhydride or fumaric acid with condensed liquid ammonia.

12. The process as claimed in claim 11, wherein the resulting reaction product is separated off.

13. A process for the preparation of a polymer with recurring succinyl units, which comprises reacting maleic anhydride, maleic acid and/or fumaric acid with condensed liquid ammonia in the presence of comonomers.

14. The process as claimed in claim 13, wherein the product obtained after the reaction is hydrolyzed with a base.

15. The process as claimed in claim 13, wherein the reaction is carried out in liquid ammonia at 60° to 100° C. under a pressure of 26 to 64 bar.

16. The process as claimed in claim 1, wherein the polymerization is carried out at 120° to 220° C.

17. The process as claimed in claim 13, wherein the polymerization is carried out at 100° to 350° C.

18. The process as claimed in claim 10, wherein the resulting polymer has a molecular weight of 500 to 6,000 Mw as measured by gel permeation chromatography.

19. The process as claimed in claim 13, wherein the resulting polymer has a molecular weight of 500 to 10,000 Mw as measured by gel permeation chromatography.

20. The process as claimed in claim 14, wherein the resulting polymer has a molecular weight of 500 to 6,000 Mw as measured by gel permeation chromatography.

* * * * *